US00PP21911P3

(12) United States Plant Patent
Sonoda

(10) Patent No.: US PP21,911 P3
(45) Date of Patent: May 10, 2011

(54) *MANDEVILLA* PLANT NAMED 'KAMISHINDENPINK5005'

(50) Latin Name: *Mandevilla. Lindl.*
Varietal Denomination: Kamishindenpink5005

(76) Inventor: Norio Sonoda, Kagoshima (JP)

( * ) Notice: Subject to any disclaimer, the term of this patent is extended or adjusted under 35 U.S.C. 154(b) by 0 days.

(21) Appl. No.: 12/588,098

(22) Filed: Oct. 2, 2009

(65) Prior Publication Data

US 2011/0083237 P1 Apr. 7, 2011

(51) Int. Cl.
*A01H 5/00* (2006.01)

(52) U.S. Cl. ..... Plt./226

(58) Field of Classification Search ..... Plt./226
See application file for complete search history.

*Primary Examiner* — Annette H Para

(74) *Attorney, Agent, or Firm* — Westerman, Hattori, Daniels & Adrian, LLP

(57) ABSTRACT

A new and distinct *Mandevilla* plant denominated 'Kamishindenpink5005'. It has upright and vining plant habit, relatively small glossy foliage, freely branching habit, freely flowering habit. The plant is in full flower around Mother's Day.

3 Drawing Sheets

Latin name of the genus and species: *Mandevilla sanderi* (Hemsl.)

All content of Japanese application No. 22764, filed on Jul. 17, 2008 is incorporated herein by reference.

BACKGROUND OF THE INVENTION

In May, 2003, to obtain this variety, a pink-based nameless variety of a culture line possessed by Applicant was crossbred with mixed pollens of nameless varieties of a culture line possessed by Applicant in a farm owned by Applicant in Yusui-cho, Aira-gun, Kagoshima, Japan. Compared to 'Kamishindenpink5005', the pink-based nameless variety had reversely facing petals at the time of blooming. The mixed pollens of nameless varieties were obtained from several varieties such as a rose-colored variety, a white-colored variety and a pink-colored variety.

In February, 2004, a plant was grown through the above crossbred and a resultant seed from the plant was planted in soil on the farm owned by Applicant in Yusui-cho, Aira-gun, Kagoshima, Japan, to grow (germinate) and then bloom. This planting was carried out to expect that some varied plant could be obtained.

In April, 2005, from several hundreds of the flowering plants by the above planting, one individual plant having good-colored flowers appeared. Then, the individual plant was selected and a branch (stem) thereof was removed and inserted in soil on the farm owned by Applicant in Yusui-cho, Aira-gun, Kagoshima, Japan, to grow (cutting, i.e., vegetative reproduction) and such a vegetative reproduction was repeated for propagation.

In June, 2006, the culture was completed after ensuring uniformity and stability. In other words, it was confirmed that the plant having good-colored flowers, which was 'Kamishindenpink5005', could be obtained with uniformity and stability, and the above repetition was completed.

SUMMARY OF THE INVENTION

1. Upright and vining plant habit.
2. Relatively small glossy foliage.

3. Freely branching habit.
4. Freely flowering habit.
5. Being in full flower around Mother's Day.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Mandevilla.*

DETAILED BOTANICAL DESCRIPTION

Figure 1:
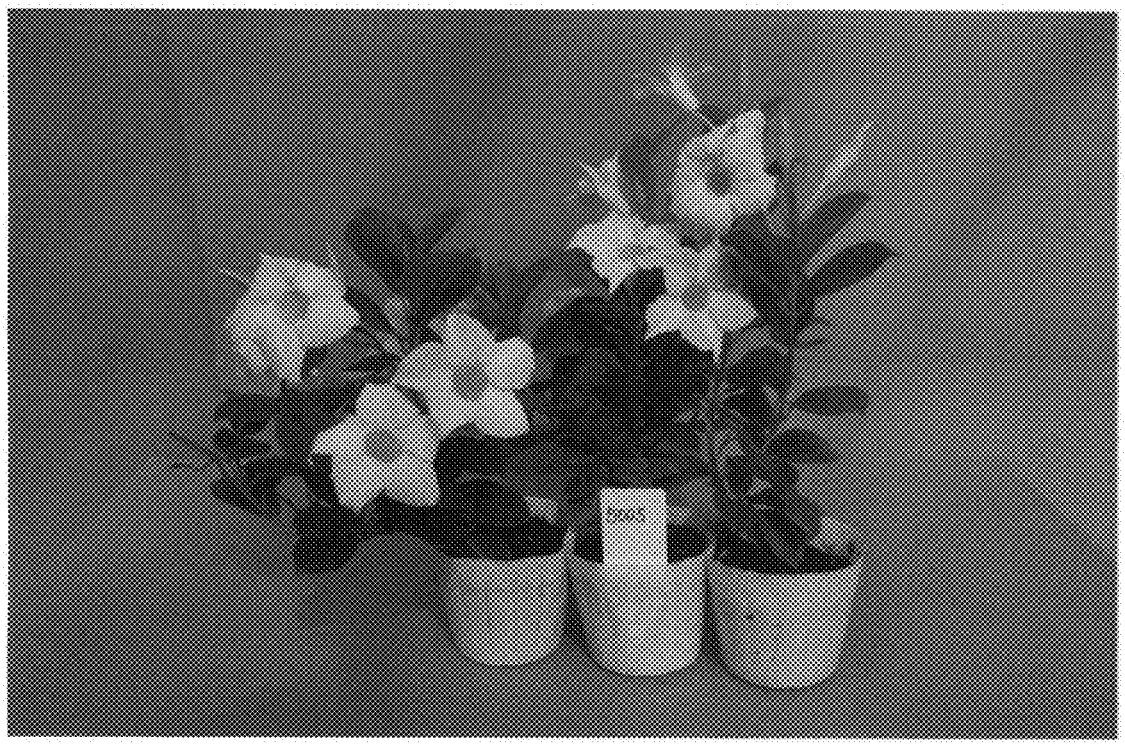
FIG. 1 is a view of the plant body, wherein the plant is 14 months old after the above insertion in a soil of the branch.
Figure 2:
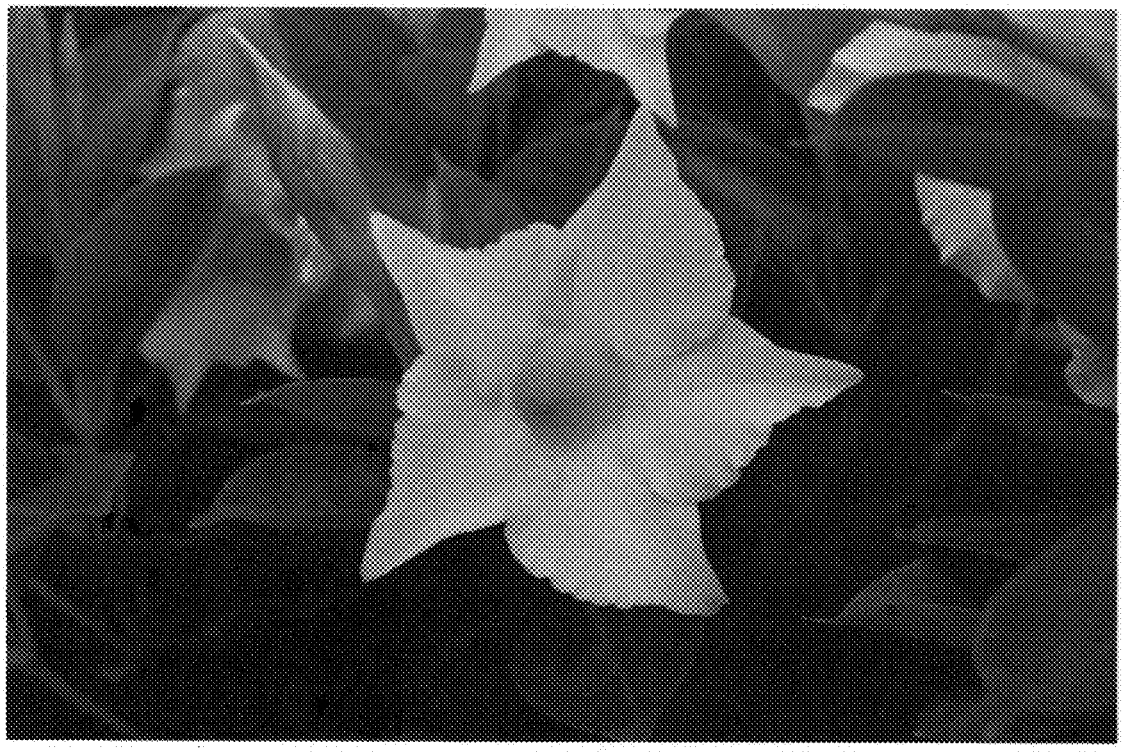
FIG. 2 is a close-up view of the flower, wherein the plant is 14 months old after the above insertion in a soil of the branch.
Figure 3:
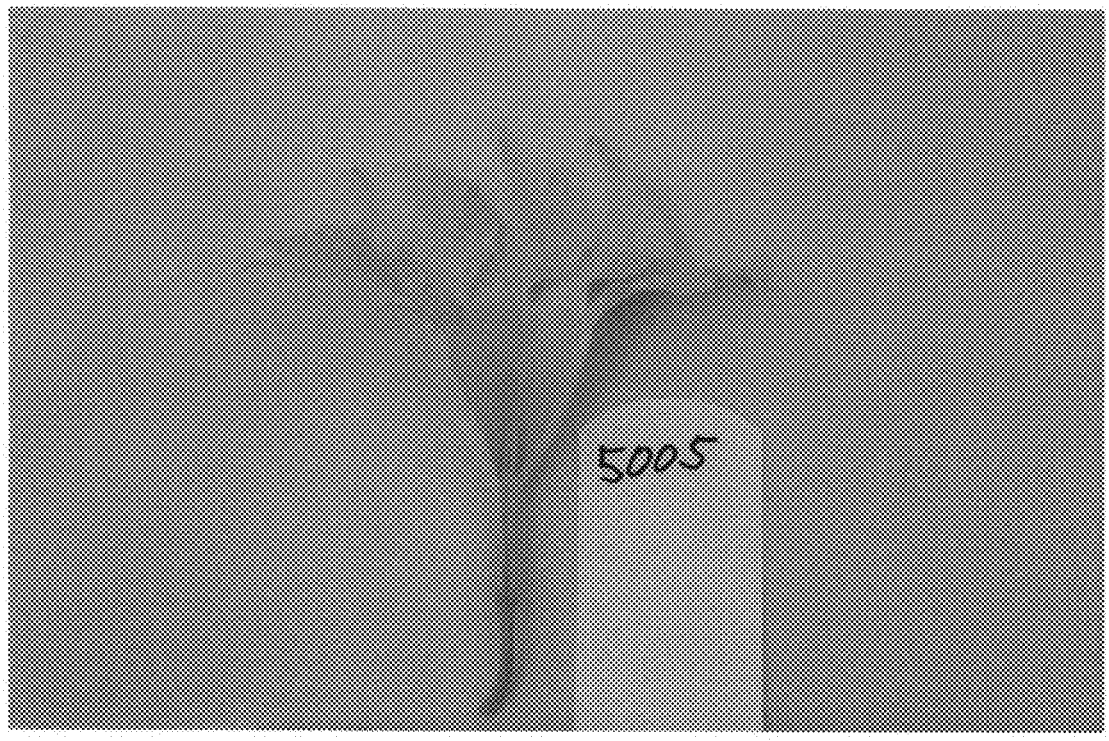
FIG. 3 is a diagrammatic view of the plant's flower, wherein the plant is 14 months old after the above insertion in a soil of the branch.
Figure 4:
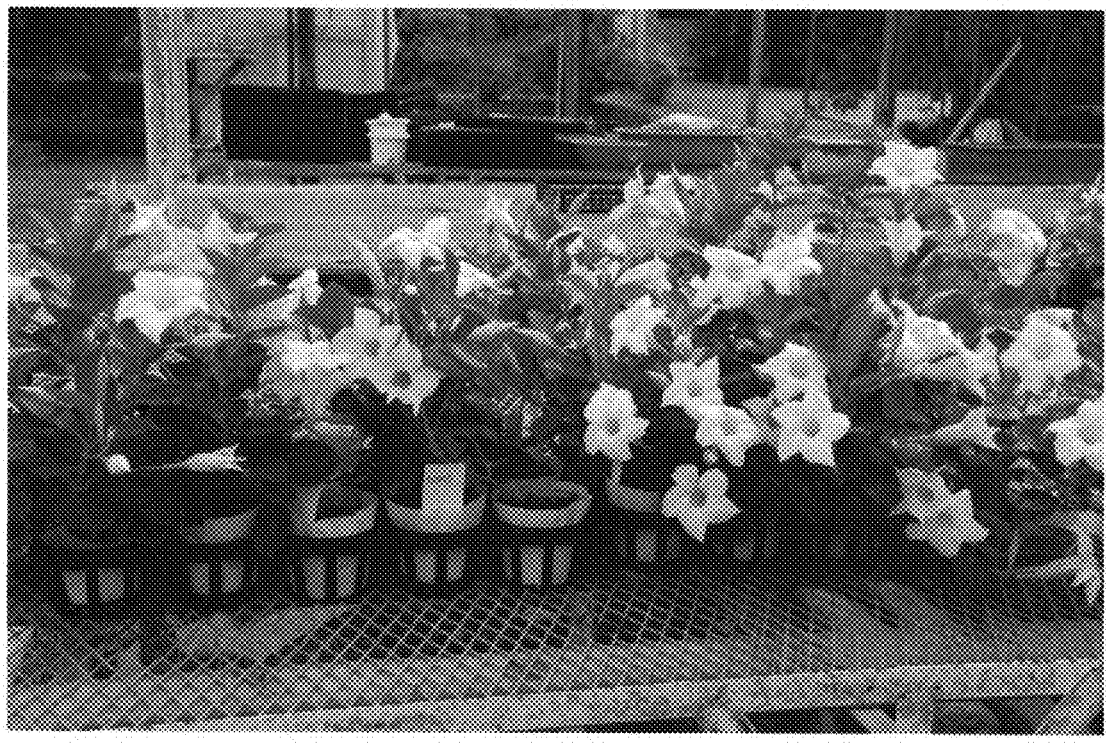
FIG. 4 is a panoramic view of the cultivation area.
Figure 5:
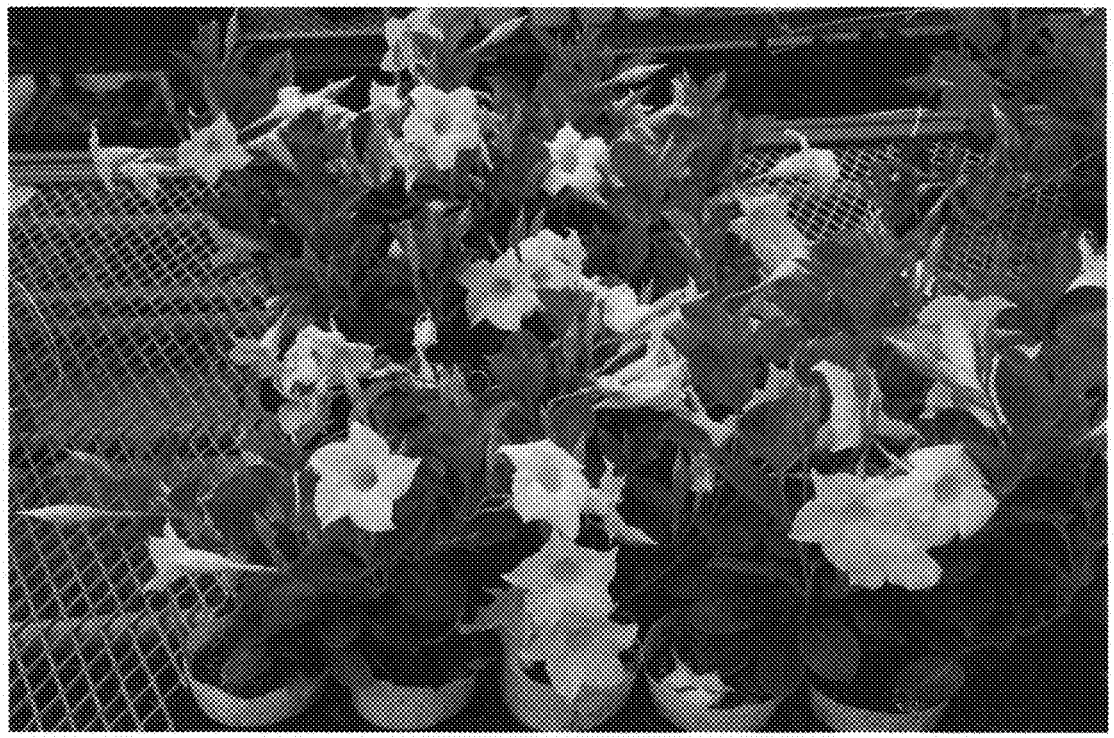
FIG. 5 is another panoramic view of the cultivation area.

In the following description, color references are made to Japan Horticulture Standard Color Chart, edited as the 2nd print, resale on Sep. 10, 1997, except where general terms of ordinary dictionary significance are used. Plants used for the aforementioned photographs and following description were grown under conditions which closely approximate commercial production conditions during the early summer in a polyethylene-covered greenhouse in Yusui-cho, Aira-gun, Kagoshima in Japan. During the production of the plants, day temperatures averaged 26° C., and night temperatures averaged 14° C.

Propagation:

*Type.*—By vegetative cuttings.

*Time to initiate roots.*—About three weeks at 23° C. to 26° C.

*Time to produce a rooted young plant.*—About 40 days at 23° C. to 26° C.

*Root description.*—Fibrous, fleshy, white in color.

*Rooting habit.*—Freely branching.

Plant description:

*Form.*—Perennial. Upright and vining plant habit. Vigorous growth habit.

*Plant height.*—About 43 cm.

*Lateral branch description.*—Length: About 43 cm.

*Diameter.*—About 1.5 mm. Internode length: About 2.5 cm. Strength: Strong. Texture: Smooth, glabrous. Color, young: Close to Color Chart No. 3307. Mature: Close to Color Chart No. 1309.

Foliage description:

*Arrangement.*—Opposite, simple.

*Length.*—4.5 cm.

*Width.*—2.75 cm.

*Shape.*—Elliptic.

*Apex.*—Cuspidate.

*Base.*—Cordate.

*Margin.*—Entire.

*Texture, upper and lower surfaces.*—Smooth, glabrous.

*Luster, upper and lower surfaces.*—Glossy.

*Venation pattern.*—Pinnate, reticulate.

*Color.*—Developing foliage, upper surface: Close to Color Chart No. 3508. Developing foliage, lower surface: Close to Color Chart No. 3508. Fully expanded foliage, upper surface: Close to Color Chart No. 3509, Venation, Close to Color Chart No. 3507. Lower surface: Close to Color Chart No. 3508, Venation, Close to Color Chart No. 3508.

*Petiole length.*—About 0.8 cm.

*Petiole diameter.*—About 0.2 cm.

*Petiole texture, upper and lower surfaces.*—Sparsely pubescent.

*Petiole color, upper and lower surfaces.*—Close to Color Chart No. 3507.

Flower description:

*Flower type and habit.*—Single salver form flowers; flowers racemose; flowers face mostly outwardly, freely flowering habit, about five flowers per inflorescence.

*Natural flowering season.*—Long flowering period; Fully flowering from late spring to early summer in Japan; Reduced flowering in midsummer, and then be in a flowering period again in late autumn.

*Flower longevity on the plant.*—Ten to fourteen days. Flowers not persistent.

*Fragrance.*—Not detected.

*Inflorescence length.*—8.0 cm.

*Inflorescence diameter.*—8.5 cm.

*Flowers.*—Appearance: Flared trumpet, corolla fused, five-parted; petals slightly imbricate; flowers roughly star-shaped. Diameter: 8.0 cm. Depth (length): 5.5 cm. Throat diameter: About 2.5 cm. Tube length: 5.5 cm. Tube diameter, mid-section: 1.8 cm. Tube diameter, base: About 3 mm.

*Flower buds.*—Height: About 5.3 cm. Diameter: About 1.2 cm. Shape: Lenticular. Color: Close to Color Chart No. 9704.

*Corolla.*—Arrangement/appearance: Single whorl of five petals, fused into flared trumpet; petals slightly imbricate. Petal length: About 3.7 cm. Petal width: About 3.0 cm. Petal shape: Spatulate. Petal apex: Acuminate. Petal margin: Entire, slightly undulate. Petal texture, upper and lower surfaces: Smooth, glabrous, velvety. Color: Petal, when opening and fully opened, upper surface: Close to Color Chart No. 9702; Lower surface: Close to Color Chart No. 9503.

*Sepals.*—Arrangement/appearance: Five per flower in a single whorl; fused. Length: About 10 mm. Width: About 5 mm. Shape: Lanceolate. Apex: Acute. Margin: Entire. Texture, upper and lower surfaces: Smooth, glabrous. Color, immature, upper and lower surfaces: Close to Color Chart No. 3704; towards the apex, close to Color Chart No. 0405. Color, mature, upper and lower surfaces: Close to Color Chart No. 3704; towards the apex, close to Color Chart No. 0405.

*Peduncles.*—Length: About 8.0 cm. Diameter: About 3.5 mm. Texture: Smooth, glabrous. Strength: Flexible, but strong. Color: Close to Color Chart No. 3507.

*Pedicels.*—Length: About 1.8 cm. Diameter: 3 mm. Texture: Smooth, glabrous, flexible, but strong. Color: Close to Color Chart No. 3507.

*Reproductive organs.*—Stamens: Quantity/arrangement: Typically five; filament fused to corolla; anthers, connivent. Anther shape: Elliptic. Anther size: About 8 mm by 1 mm. Anther color: Close to Color Chart No. 2505. Pollen amount: Scarce. Pollen color: Close to Color Chart No. 2506. Pistils: Quantity: Typically one. Pistil length: About 2.2 cm. Stigma shape: Conical. Stigma color: Close to Color Chart No. 3506. Ovary color: Close to Color Chart No. 3506.

*Seed/fruit.*—Seed and fruit production has not been observed.

Disease/pest resistance: Plants of the new *Mandevilla* have not been noted to be resistant to pathogens and pests common to *Mandevilla*.

Temperature tolerance: Plants of the new *Mandevilla* have been observed to tolerate temperatures from about 5° C. to about 37° C.

The 'Kamishindenpink5005' has a white-colored flowers (but not pure white) and a good contrast compared to the Applicant's other varieties such as 'Hannyajisenred6106' (U.S. application Ser. No. 12/588,097), 'Tsukiakaripink6030'(U.S. application Ser. No. 12/588,096), 'Kedoaka5152'(U.S. application Ser. No. 12/588,099), and 'Sawaranored5134'(U.S. application Ser. No. 12/588,100).

What is claimed is:

1. A new and distinct *Mandevilla* plant named 'Kamishindenpink5005' as illustrated and described.

* * * * *